United States Patent [19]

Day et al.

[11] Patent Number: 5,006,661

[45] Date of Patent: Apr. 9, 1991

[54] SELECTIVE STEREOSPECIFIC BIOLOGICALLY ACTIVE BETA-LACTAMS

[75] Inventors: Richard A. Day, Cleves, Ohio; John Wallace, Covington, Ky.

[73] Assignee: University of Cincinnati, Cincinnati, Ohio

[21] Appl. No.: 382,531

[22] Filed: Jul. 19, 1989

Related U.S. Application Data

[62] Division of Ser. No. 62,856, Jun. 16, 1987, Pat. No. 4,855,419.

[51] Int. Cl.$^5$ .......................................... C07D 263/04
[52] U.S. Cl. .................................. 548/227; 540/310
[58] Field of Search ......................... 548/227; 540/310

[56] References Cited

U.S. PATENT DOCUMENTS

| | | | |
|---|---|---|---|
| 3,644,412 | 2/1972 | Fujimoto et al. | 548/227 |
| 3,658,788 | 4/1972 | Orgel et al. | 260/211.5 R |
| 3,989,685 | 11/1976 | Tanida et al. | 260/239.1 |
| 3,994,883 | 11/1976 | Borrenang et al. | 260/243 C |
| 4,020,077 | 4/1977 | Cook et al. | 260/306.7 C |
| 4,051,132 | 9/1977 | Firestine | 544/20 |
| 4,072,677 | 2/1978 | Callander | 260/239.1 |
| 4,111,933 | 9/1978 | Eckert et al. | 260/239.1 |
| 4,167,630 | 9/1979 | Firestine | 544/90 |
| 4,248,966 | 2/1981 | Demain et al. | 435/43 |
| 4,251,442 | 2/1981 | Worito et al. | 260/239.1 |
| 4,301,282 | 11/1981 | Katner | 544/90 |
| 4,307,192 | 12/1981 | Demain | 435/47 |
| 4,314,062 | 2/1982 | Lund | 544/402 |
| 4,320,055 | 3/1982 | Blasczak | 260/239.1 |
| 4,452,796 | 6/1984 | Barth | 424/246 |
| 4,536,393 | 8/1985 | Barth | 424/114 |
| 4,565,820 | 1/1986 | Schmur et al. | 548/227 |
| 4,689,336 | 8/1987 | Schnur | 548/227 |
| 4,946,942 | 8/1990 | Fuller et al. | 548/227 |

FOREIGN PATENT DOCUMENTS

88/10256 12/1988 World Int. Prop. O. .

OTHER PUBLICATIONS

Hamilton-Miller, An Historical Introduction to $\beta$-Lactamase, J. T. Smith (ed), Arademio Oness, (1979), N.Y.
Day et al., FEBS Letters, vol. 193, No. 2, pp. 145-149, (1985).
Sheehan et al., JACS, vol. 79, pp. 1262-1263, (1957).
Sheehan et al., JACS, vol. 81, pp. 3089-3094, (1959).
Cephalosporius and Benicellins, pp. 259-260, Edited by Edurn Flynn, (1972), Academic Press.

*Primary Examiner*—Nicholas S. Rizzo
*Attorney, Agent, or Firm*—Frost & Jacobs

[57] ABSTRACT

The present invention relates to a method for producing novel 4-[1-oxoalkyl]-2,5-oxazolidinediones, (4-1 OOD), and their use in a stereoselective method of producing beta-lactam-containing compounds which include several biologically active compounds such as the well-known families of pencillin and cephalosporin antibiotics. The method of the present invention involves generally the reaction of the above-described 4-[1-oxoalkyl]-2,5-oxazolidinediones so produced with a thiol amine having a geometry amenable to forming the precursor of the desired beta-lactam-containing compound or, in one scheme, forming the beta-lactam-containing compound itelf directly. This is done either by direct reaction of the 4-1 ODD with a thiol amine (which by one pathway proceeds directly to the beta-lactam-containing compound) or by first converting the 4-1 OOD to its 2-[1-oxoalkyl]-2-amino acid form before its reaction with the thiol amine; and then forming the beta lactam by action of cyanogen). The beta-lactam-containing compounds can be further modified according to methods known in the art to produce specific derivatives as desired.

2 Claims, No Drawings

SELECTIVE STEREOSPECIFIC BIOLOGICALLY ACTIVE BETA-LACTAMS

This is a division, of application Ser. No. 07/062,856, filed Jan. 16, 1987, U.S. Pat. No. 4,855,419.

I. FIELD OF THE INVENTION.

The present invention relates to a method for producing novel 4-[1-oxoalkyl]-2,5-oxazolidinediones, (4-1 OOD), and their use in a stereoselective method of producing beta-lactam-containing compounds which include several biologically active compounds such as the well-known families of penicillin and cephalosporin antibiotics.

The method of the present invention involves generally the reaction of the above-described 4-[1-oxoalkyl]-2,5-oxazolidinediones so produced with a thiol amine having a geometry amenable to forming the precursor of the desired beta-lactam-containing compound or, in one scheme, forming the beta-lactam-containing compound itself directly. This is done either by direct reaction of the 4-1 OOD with a thiol amine (which by one pathway proceeds directly to the beta-lactam-containing compound) or by first converting the 4-1 OOD to its 2-[1-oxoalkyl]-2-amino acid form before its reaction with the thiol amine; and then forming the beta lactam by action of cyanogen). The beta-lactam-containing compounds can be further modified according to methods known in the art to produce specific derivatives as desired.

II. BACKGROUND OF THE INVENTION.

The usefulness and importance of biologically active compounds which contain beta-lactam bonds is well established. This class of compounds includes the well-known penicillin and cephalosporin families of antibiotics. The synthetic production of these compounds presents many of the problems normally attendant to complex organic synthesis which include the challenge of designing a synthetic strategy to maximize yield of the desired product. As a general rule, it is desirable to find synthetic strategies which will minimize the number of synthetic steps and to have those synthetic steps, where possible, favor the production of the desired compound having the desired isomeric form where more than one such isomeric form exists. This is especially critical to the synthetic production of biologically active compounds whose activity very often depends on the compound's stereoisomerism.

Because of the delicate nature of biologically active compounds (or their precursors), the synthesis of these compounds is most advantageously carried out under mild reaction conditions. Mild reaction conditions can also be important in preventing unwanted side reactions as well as preventing the racemization of products from stereoselective synthetic steps.

In particular, the production of the biologically active compounds (i.e. penicillin and cephalosporin antibiotics and the like) presented here presents two problems. The first problem is the stereoselective formation of the precursor by the reaction of a carbonyl group (i.e. the carbonyl pended at the 4-position of the 2,5-oxazolidinedione) with a suitable thiol amine. The second problem is that a carboxylic acid moiety must be available to form an intramolecular beta-lactam bond while maintaining the desired stereochemistry of the final product.

In addition, it is desirable to develop synthetic strategies which produce fewer steps and by-products in order to avoid unwanted side reactions, as well as to produce a purer product without extensive filtration or recrystalization.

Several methods of producing compounds in the penicillin and cephalosporin families are already known in the art. Examples include Sheehan, J. C. and Henery-Logan, K. R. *The Total and Partial General Synthesis of The Penicillins*, J. Am. Chem. Soc., Vol. 81, pp. 2983-2990 (1961); Aizpurua, J. M. et al., *A Convenient Synthetic Approach to Alpha-Amino-Beta-Lactam Synthesis Promoted By Phenol Diclorophosphate Reagent*, Tetrahedron Letters, Vol. 25, No. 35, pp. 3905-3908 (1984); Evans, D. A. and Sjogren, E. B., *The Asymmetric Synthesis of BetaLactam Antibiotics - I Application of Chiral Oxazolidones in the Staudinger Reaction*, Tetrahedron Letters, Vol. 26, No. 32, pp. 3783, 3786 (1985); Evans, D. A. and Sjogren, E. B., *The Asymmetric Synthesis of Beta- Lactam Antibiotics - II The First Enantio Selective Synthesis of the Carbacephalosporin Nucleus*, Tetrahedron Letters, Vol. 26, No. 32, pp. 3787-3790 (1985); and Wei, C. C., *Synthesis of Chiral Beta-Lactams Using L-Ascorbic Acid*, J. Org. Chem., Vol. 50, pp. 3462-3467 (1985). An example of a cephalosporin synthesis is contained in Woodward et al, *Total Synthesis*, J. Am. Chem. Soc. 88, 852 (1966). A review of cephalosporin C and related compounds is also contained in Abraham, Quart. Rev. Chem. Soc. 21, 231 (1967). A general resource material on these types of syntheses is Coppola, G. M. and Schuster, H. F. *Asymmetric Synthesis: Construction of Chiral Molecules Using Amino Acids*, John Wiley & Sons (1987). All of the above publications are incorporated herein by reference.

The synthetic pathways described in these and other prior art references typically involve a multi-step synthesis (i.e. typically more than 10 steps) which produce many varied by-products and always involve the extensive utilization of blocking groups to prevent unwanted side reactions and direct the synthesis towards the desired product.

It has now been found that the novel 4-[1-oxoalkyl]-2,5-oxazolidinediones can be applied in a variety of synthetic schemes to accomplish the desired stereoselective synthesis via a small number of synthetic steps without the need for the extensive use of blocking groups to protect reactive moieties of the precursors (i.e. the lactam-forming amino group) during preceeding synthetic steps (i.e. the thiazolidine-forming step). Furthermore, the small amount of "blocking" which is done in the method of the present invention produces relatively small amounts of non-containing by-products. The method of the present invention can be carried out under mild reaction conditions to prevent loss of product due to the decomposition or racemiziation, resulting in relatively high end product yields.

III. SUMMARY OF THE INVENTION.

The present invention relates both to the preparation of 4-[1-oxoalkyl]-2,5-oxazolidinediones and to their use in synthetic pathways for the stereoselective formation of biologically active beta-lactams, including those in the penicillin and cephalosporin family of antibiotics.

Formation of the 4-[1-oxoalkyl 2,5-oxazolidinediones

The formation of the 4-[1-oxoalkyl]-2,5-oxazolidinediones is accomplished by the reaction of one of the 2,5-oxazolidinediones (commonly known as Leuchs anhydrides) with an ester and at least one metal hydride according to the following formula:

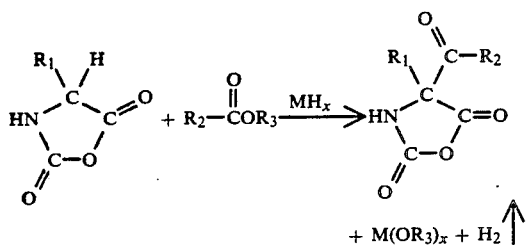

wherein $R_1$ and $R_2$ are selected from the group consisting of hydrogen, aryl, aralkyl and saturated and unsaturated alkyl groups, and $R_3$ is selected from the group consisting of aryl, aralkyl and saturated and unsaturated alkyl groups; and M is a metal in a metal hydride, such as an alkali or alkaline metal hydride and wherein represents the stoichiometric value for the individual hydride equal to the charge on the M acetal.

Examples of the oxazolidinediones which may be applied in the above reaction include 2,5-oxazolidine dione, 4-methyl-2,5-oxazolidinedione, 4-benzyl-2,5-oxazolidinedione and 4-ethenyl-2,5-oxazolidinedione.

Examples of esters used in accordance with the invention include t-butylformate, t-butylacetate, ethylacetate, and ethylformate. Among these, t-butylformate is preferred for production of penicillins and cephalosporins.

Some examples of the metal hydrides used in the above reaction include: potassium hydride, sodium hydride and calcium hydride. The preferred metal hydride is sodium hydride.

The reaction may be carried out in any appropriate apolar aromatic solvents, including toluene, benzene, xylene, ethyl benzene, or in mixed apolar aromatic solvent compositions. Of these, toluene is preferred. The temperature of the reaction should be maintained below the decomposition point of the reactants; normally at about reflux temperature. The preferred temperature range is from about 25° C. to about the reflux temperature of the reaction mixture.

Synthesis of Beta-Lactam-Containing Compounds.

The product oxazolidinediones can be applied in the stereoselective synthesis of beta-lactam-containing biologically active compounds, such as those in the penicillin and cephalosporin families of antibiotics. This is done according to two distinct viable schemes, all of which ultimately involve (1) the reaction of the side chain carboxyl group (i.e. on the 4 position) with both the thiol and amine groups of a thiol amine compound and (2) the further reaction of the 5-position carboxyl group with the amine group of the thiol amine to form the beta-lactam ring.

This reaction occurs in stepwise fashion in Scheme I while proceeding directly to the beta-lactam product in Scheme II.

Additional modification of the beta-lactam product can be done according to methods known in the art in order to produce specific derivatives as desired. Such modifications may include eliminations, substitutions or additions. An example of such a modification is acylation.

A basic representation of this reaction is as follows:

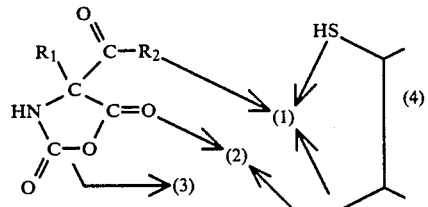

(1) condensation of the carboxyl 4-position of the substituent with the thiol amine;
(2) beta-lactam ring closure;
(3) loss of $CO_2$;
(4) Balance of molecule need only have proper geometry amenable to reaction and ring formation, and hold side groups where desired, either in the final biologically active product or precursor thereof (i.e., the geometry of the example results in a five-membered ring although other geometries are possible).

A specific representative complete conversion is:

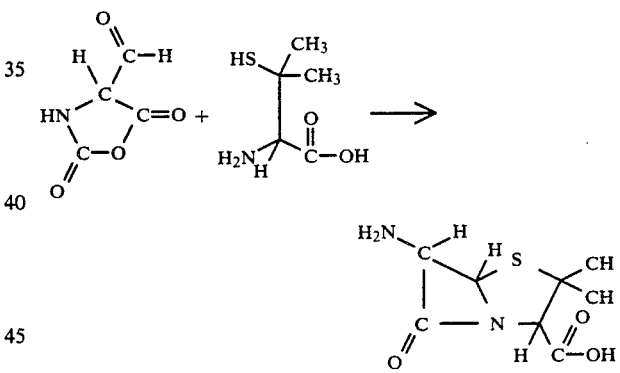

Scheme I

Scheme I comprises generally the conversion of the 4(1-oxoaklyl)-2,5-oxazolidinedione (I) to its 2(1-oxalkyl)-2-amino acid form (II) by exposure to a mildly acidic environment (Step 1). This is followed by the reaction of the amino acid form with the thiol amine (shown below as D-penicillamine) (III) to form the intermediate thiazolidine (IV) (Step 2) which in turn is converted to the beta-lactam-containing produce (IV) by action of cyanogen to effect ring closure (Step 3). Scheme I may be represented as follows:

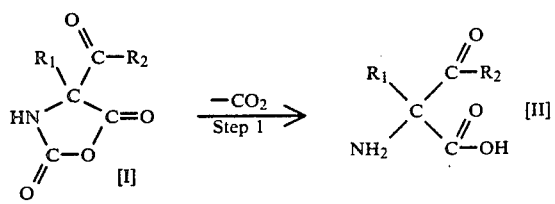

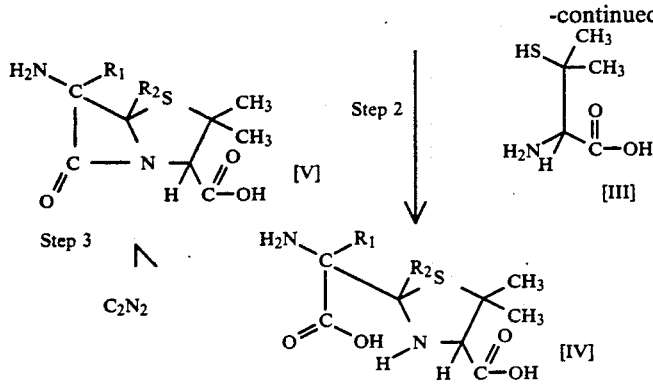

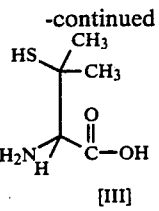

Although shown as two distinct chemical conversions, Step 1 and Step 2 occur in the same procedural phase and under like reaction and conditions.

The first step of Scheme I involves the reaction of the isolated 4-1OOD as follows:

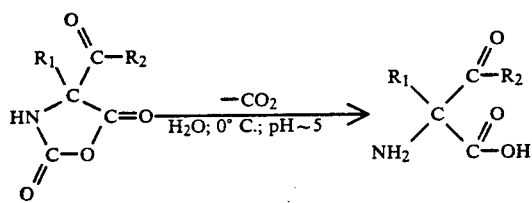

The cyclic anhydrides used in this reaction are of the general formula:

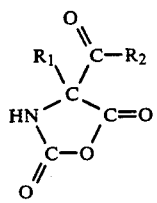

wherein $R_1$ and $R_2$ are independently selected from the group consisting of hydrogen, aryl, aralkyl and saturated and unsaturated alkyl groups. The preferred cyclic anhydride of this group is where both $R_1$ and $R_2$ are hydrogen.

The solvent compositions which may be used in Step 1 are generally aqueous or partially aqueous depending on the solubility of the reactant and products. Examples of such solvent compositions include 70–90% dimethylformamide /10%–30% water (v/v) and 70%–90% dimethylsulfoxide (DMSO) /10%–30% water (v/v). The preferred solvent may vary with the solubility of the reactants, although 70% dimethylformamide 30% water has been found to work well in most applications.

The thiol amine compound used in Step 2 is selected generally from those which are amenable to the formation of the five-and six-membered geometries in the final product. The thiol amine precursors for five- and six-membered ring formation are therefore the thiol amines in which the amine group is separated from the thiol group by 2 or 3 carbons, respectively. The thiol amines used in accordance with the invention are described by the following general formulae:

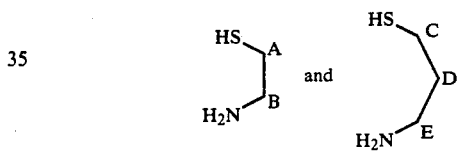

wherein sites A, B, C, D and E are saturated sites and wherein the substituents on these sites are independently selected from the group consisting of hydrogen, saturated and unsaturated alkyl groups, and carboxyl groups.

Examples of such compounds include D-penicillamine and 3-aminopropanethiol.

Step 2 may be represented generally as follows:

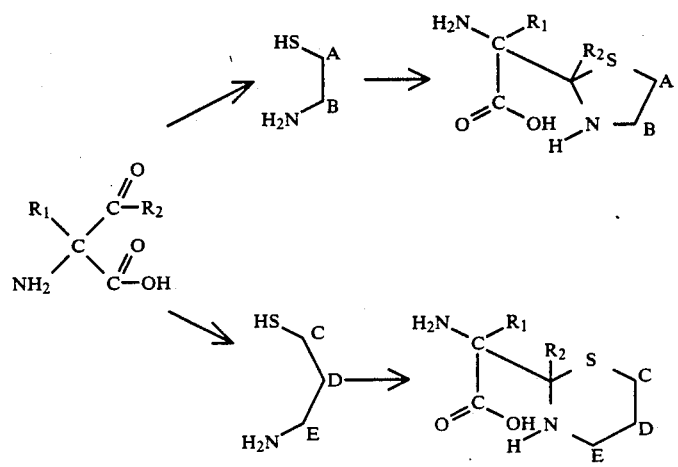

The Step 1/Step 2 phase may be promoted by stirring and is generally complete within a period varying from 10 minutes to several hours.

Step 3 concludes the synthesis with the formation of the beta-lactam ring by reaction of the thiazolidine intermediate with cyanogen gas ($C_2N_2$), as follows:

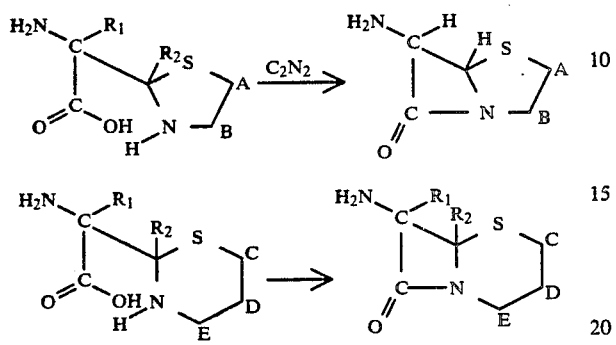

The reaction temperature parameters of this Step are the same as in Steps 1 and 2 above.

The pH, however, should be maintained in the same range of from about 5 to about 6, preferably about 6 and may be adjusted by the addition of mineral acids on bases as needed.

The cyanogen gas is brought into contact with the reaction solution by placing a quantity of the gas over the solution in a sealed vessel. The amount of cyanogen used may be varied between stoichiometric and ten-fold excess, although amounts nearer the former are preferred. The reaction vessel may be agitated or the contents stirred to promote reaction. The reaction occurs relatively rapidly and is completed normally within 6 to 8 hours, although some reactions have been found to require reaction times of up to about 24 hours.

Scheme II

The second scheme by which beta-lactam-containing compound can be formed involves generally reacting a cyclic anhydride (which already contains a carbonyl group at the 4-position) directly with a thiol amine compound having the proper geometry for formation of the beta-lactam-containing compound. In this scheme, the beta-lactam-containing compound forms directly without the need to convert the 4-1 OOD to the amino acid form. Also, there is no need to use cyanogen gas to form the beta-lactam ring as this occurs spontaneously as indicated below.

The cyclic anhydrides and thiol amines which may be used in Scheme II are the same as those described in Scheme I above.

Scheme II reactions may be carried out in any suitable multiple-component organic solvent which has a relatively high nucleophilic/electrophilic character and which is neither too strongly acidic nor too basic. An example of a suitable multi-component solvent composition is pyridine/acetic acid (1:1). The addition of a small amount of water (approximately 10–30% by volume of the total solvent composition) is often required to dissolve the reactants.

The measured pH of the reaction solution should be maintained in the range of from about 5 to about 6, and preferably about 5.

The reaction temperature is maintained in the range of from about 0° C. to about 40° C., a preferred range being from about 0° C. to about 25° C. The most preferred temperature is about 0° C.

It has also been found that when Scheme II-type reactions are conducted, under otherwise like reaction conditions, in solvents having relatively low nucleophilic/electrophilic character, a substantial portion of the product remains as the intermediate anhydride-thiol amine adduct represented by the following general formulae:

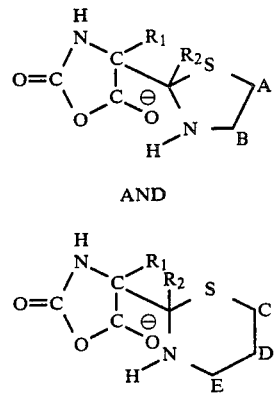

AND wherein $R_1$, $R_2$ and A-E are as defined above. These intermediates normally exist as an anion in a salt pair having at least one negative charge which is believed to be centered about carbons 4 and 5 of the anhydride portion of the intermediate.

This intermediate is isoable and can be further converted to the corresponding beta-lactam-containing product by exposure to a solvent composition of relatively high nucleophilic/electrophilic character. As mentioned above, and example of such a suitable solvent composition is pyridine/acetic acid (1:1). This conversion can be performed under the same time, temperature and pH parameters mentioned above for the direct beta-lactam-forming Scheme II reaction.

The conversion of the intermediate to the beta-lactam product can be improved by the treatment of the reaction mixture with cyanogen gas in the same ranges of amounts and reaction conditions as in Scheme I above.

The cyclic anhydrides and thiol amines which may be used in Scheme II are the same as those described in Scheme I above.

Scheme II reactions may be carried out in any suitable multiple-component organic solvent which has a relatively high nucleophilic/electrophilic character and which is neither too strongly acidic nor too basic. An example of a suitable multi-component solvent composition is pyridine/acetic acid (1:1).

The measured pH of the reaction solution should be maintained in the range of from about 5 to about 6, and preferably about 5.

The reaction temperature is maintained in the range of from about 0° C. to about 40° C., a preferred range being from about 0° C. to about 25° C. The most preferred temperature is about 0° C.

Scheme III

The third scheme for the production of beta-lactam-containing compounds parallels Scheme I with the exception that the 2-(oxoalkyl)-2-amino acid is formed directly from its unprotected amino acid precursor as follows:

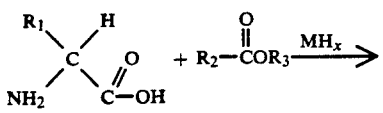
+ $R_2-\overset{O}{\overset{\|}{C}}OR_3$ $\xrightarrow{MH_x}$

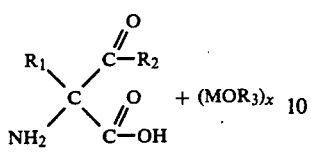
+ $(MOR_3)_x$ wherein $R_1$, $R_2$ and $R_3$ are defined as in Scheme I above and M and x are as defined in the section relating to the formation of the 4-(oxoalkyl)-2,5 oxazolidinediones above.

The amino acids used in Scheme III are selected from the group wherein $R_1$ above is selected from the group consisting of hydrogen, aryl, aralkyl and saturated and unsaturated alkyl groups. Examples of suitable amino acids include glycine, alanine, valine, leucine and phenylalanine.

Scheme III reactions may be carried out in apolar organic suitable solvents depending on the solubility of the particular precursor amino acid used. Examples include benzene, toluene and xylene. The preferred solvent is toluene.

The metal hydrides used in Scheme III are the same as those used in the formation of the 4-(oxoalkyl)-2,5 oxazolidinediones above and may be used in amounts which vary from stoichiometry to about a five-fold excess over the reactant amino acid.

The Scheme III reaction is typically maintained in the range of from about 0° C. to about 25° C. and is preferably maintained at about 0° C.

Reaction times may vary from 1 hour to several hours, most reactions being completed within 6 to 8 hours.

The 2-(oxoalkyl)-2-amino acid products of Scheme III reactions can easily be incorporated into a total beta-lactam synthesis by reacting the products first with a thiol amine and then with cyanogen as is done in Steps 2 and 3 of Scheme I above.

DESCRIPTION OF THE PREFERRED EMBODIMENTS.

The preferred embodiments are exemplified by the following examples. Substitution and variation of reactants, concentrations, temperatures and other reaction parameters disclosed herein are within the ability of one skilled in the art.

EXAMPLE 1

Synthesis of 4-(oxomethyl)-2,5-oxazolidinedione

Oxazolidine-2,5-dione (1 mmol) was suspended in a mixture of 1 ml tertiary butyl formate (1 cc) and toluene (1 cc) with exclusion of moisture by blanketing with nitrogen. Sodium hydride powder as a toluene suspension (approximately 2 to 4 mmoles in 1-2 ml toluene) was added. The suspension was warmed gently to a temperature of approximately 35° to 40° C. Before achieving reflux the evolution of hydrogen as a strong flux of fine bubbles appeared The dark gray suspension was brought to reflux. In approximately one half hour the suspension had become light gray color and the evolution of hydrogen had essentially stopped. Refluxing was continued for a total reaction time of one hour. After chilling in an ice bath, the reaction mixture was treated with an excess of glatial acetic acid; residual sodium hydride decomposed slowly giving a semi-solid, frothy, white slurry. The slurry was vacuum dried to give the crude title compound as a hygroscopic, friable white powder.

The product was characterized by conversion of an aliquot (approximately 10 mg) to its ethyl ester by brief warming (approximately 1-2 minutes) in ethanol (0.5 cc) and concentrated HCL (25 ul); the esterfication was accompanied by vigorous evolution of $CO_2$. The structure of the product was verified by mass spectroscopic analysis.

EXAMPLE 2

Synthesis of 6-Aminopenicillanic Acid from 4-(oxomethyl)-2,5-oxazolidinedione Via 2-(oxymethyl)-2-amino ethanoic acid - Scheme I Approximately 10 mmoles of 4-(oxomethyl)-2,5-oxazolidinedione was prepared in 10 cc 70% dimethyl formamide 30% water (v/v). The pH of the solution was adjusted to about 5 with concentrated hydrochloric acid (HCl) (12 $\underline{M}$). The mixture was maintained at room temperature (25° C.) and stirred for a period of 45 minutes.

The filtered product was triturated and redissolved along with 10 mmoles of D-penicillamine in another 10 cc aliquot of solvent and placed in a sealed container. These components go into solution after which a white slurry forms. Approximately a five-fold stoichiometric excess of cyanogen gas was placed in the container. The reaction container was chilled in an ice bath to a temperature of about 0° C. The slurry rapidly dissolved and the mixture darkened. The mixture was stirred for a period of about 8 hours.

The product was verified by bioassay, using non-lactamase producting *Bacillus subtilis* especially used for penicillin assays. Chromatographic characterization was effected by comparing the synthetic product with authentic 6-amino-penicillanic acid. The product was also characterized by using TLC and HPLC techniques.

EXAMPLE 3

Synthesis of 6-Aminopenicillanic Acid from 4-(oxomethyl)-oxazolidine-2,5-dione - Scheme II Approximately 10 mmoles of 4(oxomethy)-2,5-oxazolidinedione in 100 mmoles of 1:1 pyridine/glacial acetic acid (v/v) was prepared and to this was added 10 mmoles of D-penicillamine. The mixture was stirred at approximately 25° C. for a period of about six to eight hours.

The product was verified by bioassay, using non-lactamase producing *Bacillus subtilis* especially used for penicillin assays. Chromatographic characterization was effected by comparing the synthetic product with authentic 6-amino-penicillanic acid. The product was also characterized by using TLC and HPLC techniques.

EXAMPLE 4

Synthesis Of 2-[oxazolidine-2',5'-dion-4'-yl]4-carboxy-5,5-dimethyl-thiazolidine From 4-oxomethyl-2,5-oxazolidinedione - Scheme II Alternative Using Solvent Having Relatively Low Nucleophilic/Electrophilic Character Approximately 0.5 mmoles of 4-oxoamethyl-2,5-oxazolidinedione as the sodium salt of the enolate was dissolved in 1 cc of methanol. To this was added approximately 0.5 mmoles of D-penicillamine in 1 cc of 75% aqueous methanol. The resulting solution had a pH of about 5. After approximately 3 hours, a few crystals of penicillamine separated out and were removed. The solution was allowed to react for approximately 48 hours, after which the product separated out as a crystalline mass.

The product as a disodium salt was characterized by the use of mixed melting point, NMR and mass spectrometry techniques. Gentle warming of the product with an alcohol containing agency L (e.g., 1 cc methanol plus 50 ul of 6 N HEl) gave evolution of $CO_2$.

EXAMPLE 5

Synthesis Of 6-aminopenicillanic acid from 2-[oxazolidine-2',5' dion-4'-yl]-4-carboxy-5,5-dimethylthiazolidine Using Solvent Having Relatively High Nucleophilic/Electrophilic Character Approximately 3.15 mg (10.4 umoles) of the disodium salt of the product from Example 4 was dissolved by first suspending it in 500 ul of glacial acetic acid followed by the addition of 50 ul of water. After the reactant compound dissolved, about 1.5 cc of pyridine was added which produced some flocculation, but gave a clear solution having a pH of about 5 upon addition of 400 ul of $H_2O$. After standing at room temperature for 30 minutes, the material showed the presence of 6-aminopenicillanic acid (6 APA). The biological assay reference 6-aminopenicillanic acid indicated about 30–40% of the correct, biologically active isomer. This quantitation was supported by a HPLC analysis. TLC analysis confirmed the iodine staining and bleaching properties of 6-APA and its penicilloic breakdown product respectively.

EXAMPLE 6

Cyanogen Enhancement Of the Conversion Of 2-[oxazolidine-2',5'-dion-4'-yl]-4-carboxy-5,5-dimethylthiazolidine to 6-aminopenicillanic acid The reaction mixture of Example 5 was further treated with a stoichiometric excess of cyanogen gas (at 1 atm) at 0° C. gave a light amber solution which was found to give approximately a 50% yield of the alpha-isomer of 6-aminopenicillanic acid which was determined by bioassay.

EXAMPLE 7

Conversion of Unprotected Glycine Directly to 2-Amino-3-oxopropanoic Acid Sodium Salt (Penaldic acid sodium salt) - Scheme III Glycine (1 mmole) was suspended in a mixture of toluene (1 cc) and t-butyl formate (1 cc). To this was added 3 equivalents of sodium hydride (NaH) under nitrogen The mixture was brought to reflux which led to rapid evolution of H2. The reaction was complete after 15 minutes affording a yellowish, foamy, slurry. After chilling to 0° C., 200 ml of glacial acetic acid was added yielding a white suspension. The crude product was obtained under vacuum at room temperature for about 24 hours.

What is claimed is:

1. A cyclic anhydride compound having the formula:

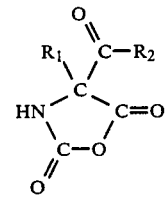

wherein $R_1$ and $R_2$ are independently selected from the group consisting of hydrogen, aryl, aralkyl and saturated and unsaturated alkyl groups.

2. A cyclic anhydride compound according to claim 1 wherein both $R_1$ and $R_2$ are hydrogen.

* * * * *